United States Patent [19]

Toyoda et al.

[11] Patent Number: 5,572,447
[45] Date of Patent: Nov. 5, 1996

[54] COORDINATE DIFFERENCE CALCULATING DEVICE

[75] Inventors: Shinjiro Toyoda; Hitoshi Ikeda; Eiri Hashimoto; Nobuaki Miyakawa, all of Kanagawa, Japan

[73] Assignee: Fuji Xerox Co., Ltd., Tokyo, Japan

[21] Appl. No.: 160,800

[22] Filed: Dec. 3, 1993

[30] Foreign Application Priority Data

Dec. 4, 1992 [JP] Japan ........................... 4-325682
Dec. 4, 1992 [JP] Japan ........................... 4-325683

[51] Int. Cl.$^6$ ..................... G01N 15/02; G01B 21/16
[52] U.S. Cl. .................... 364/561; 364/550; 364/555
[58] Field of Search ............................ 364/550, 555, 364/561, 578

[56] References Cited

PUBLICATIONS

"Fastrun: A Special Purpose, Hardwired Computer for Molecular Simulation," Proteins: Structure, Function, and Genetics, 11:242–253 (1991), Fine et al.

Primary Examiner—Edward Cosimano
Attorney, Agent, or Firm—Finnegan, Henderson, Farabow, Garrett & Dunner, L.L.P.

[57] ABSTRACT

A device for calculating differences includes a difference circuit for generating difference signals $\Delta x_j = x_j - x_i$, $\Delta y_j = y_j - y_i$, and $\Delta z_j = z_j - z_i$ between coordinates of i having $(x_i, y_i, z_i)$ coordinate signals and coordinates of j having $(x_j, y_j, z_j)$ coordinate signals in an orthogonal coordinate system. The difference circuit includes an x-axis circuit, responsive to the $x_i$ and $x_j$ signals having a first circuit for receiving the $x_i$ coordinate signal and the $x_j$ coordinate signal and generating the $\Delta x_j$; a comparison circuit for comparing the $x_i$ and $x_j$ signals and determining whether the $\Delta x_j$ is less than a first set value $-L_x/2$ corresponding to a length of a side of a virtual rectangular parallelepiped or greater than a second set value $L_x/2$ corresponding to the length of the side of the virtual rectangular parallelepiped, $L_x$ being a value indicating the length of an elongated side in the x-axis direction of the virtual rectangular parallelepiped; an adder circuit for receiving the $L_x$ and $\Delta x_j$ and adding the $L_x$ to $\Delta x_j$ when $\Delta x_j$ is less than $-L_x/2$; and a subtraction circuit for receiving the $L_x$ and $\Delta x_j$ and subtracting $L_x$ from $\Delta x_j$ when $\Delta x_j$ is greater than $L_x/2$. The difference circuit includes y-axis and z-axis circuits similar to the x-axis circuit.

11 Claims, 5 Drawing Sheets

COORDINATE DIFFERENCE CALCULATING DEVICE

BACKGROUND OF THE INVENTION

1. Field of the Invention

The invention relates to a device for calculating differences between coordinates of two particles.

2. Description of the Related Art

The field in which the behavior of a liquid, a solid, or a polymer is supposed as a result of motions of atoms constituting the substance and the motions are studied by simulating them through a computer is called molecular dynamics. In molecular dynamics, atoms or molecules are considered as particles. Forces acting between these particles are calculated, and positions where the particles are located after an elapse of time are calculated. These calculations are repeated to obtain the loci of the particles. On the basis of the obtained loci, the property, and the like of the substance are determined. In molecular dynamics, therefore, forces acting between particles are physical quantities which must be calculated.

A force acting on an i-th particle is a sum total of forces which are exerted by all particles other than the i-th particle onto the i-th particle. Since a force acting between two particles depends on the distance between the particles, it is first required to obtain the distance between the particles. When coordinates of the i-th particle are indicated by $(x_i, y_i, z_i)$ and coordinates of a j-th particle are indicated by $(x_j, y_j, z_j)$, the particle distance $r_j$ is obtained as follows:

$$r_j = \{(\Delta x_j)^2 + (\Delta y_j)^2 + (\Delta z_j)^2\}^{1/2}$$

$$\Delta x_j = x_j - x_i$$

$$\Delta y_j = y_j - y_i$$

$$\Delta z_j = z_j - z_i$$

A system in which differences are calculated by subtracting coordinates of an i-th particle from coordinates of an interested j-th particle, is known such as a difference calculating device disclosed in FASTRUN: "A Special Purpose, Hardwired Computer for Molecular Simulation", PROTEINS: Structure, Function, and Genetics 11: pp. 242–253 (1991). However, this literature teaches only that a host computer produces a pair of the interested j-th particle and the i-th particle.

However pressure, as an external force, acts on a substance. When the pressure is changed, positions of particles in the substance may be changed. When a temperature of the substance is changed, the pressure or volume of the substance may be changed. A volume change means a positional change of particles. Accordingly, for calculations in molecular dynamics, a situation where the pressure must be obtained occurs frequently. Regarding this point, the calculating device, as disclosed in the above-mentioned literature, can obtain force and energy in accordance with the pair of particles, but cannot obtain force and pressure.

Since an actual substance includes a great number (in the order of the Avogadro's number or $10^{23}$) of atoms, the computational complexity becomes so enormous that it is impossible to conduct a computer simulation using these great number of atoms as they are.

In order to comply with this, a boundary of a virtual rectangular parallelepiped is assumed in a substance, as shown in FIG. 3, and only motions of particles inside the boundary are calculated. The respective sides of the rectangular parallelepiped are determined so that the following conditions are satisfied. At first, the particle density in the rectangular parallelepiped is made equal to that of the actual substance. Next, when the distance between two particles is greater than a specific value $r_c$, it is assumed that the force acting between the particles can be neglected, and that $2r_c$ is smaller than $L_x$, $L_y$, $L_z$ (or $2r_c < L_x, L_y, L_z$). Finally, it is assumed that the actual substance can be constructed by arranging the same parallelepipeds as the above-mentioned rectangular parallelepiped in lateral and longitudinal directions. When the substance is a crystal, for example, the lengths of the sides are determined on the basis of the lattice constant. The thus determined rectangular parallelepiped is called the periodic boundary condition.

In the periodic boundary condition, it is assumed that, in the rectangular parallelepipeds surrounding and equivalent to the original rectangular parallelepiped, atoms are arranged in the exactly same configuration as that of the original rectangular parallelepiped. This is two-dimensionally illustrated in FIG. 4. Specifically, with respect to particle $j_0$ of the original rectangular parallelepiped, particles $j_1$ to $j_8$ surround particle $j_0$. When a force which is exerted by particle j onto particle i is to be calculated, only one among particles $j_0$ to $j_8$ which is nearest to particle i is required to be considered, because $2r_c < L_x, L_y, L_z$ and hence it is possible for only one of particles $j_0$ to $j_8$ to be separated from particle i by a distance shorter than $r_c$.

Actually, as shown in FIG. 5, the number of rectangular parallelepipeds surrounding the original rectangular parallelepiped is 26. Therefore, it is required that the particle which is nearest to particle i is selected from particle, and 26 reflected images of the particle j and the difference between coordinates of the selected one and those of particle i is obtained. Generally, the process of obtaining such a difference by software requires enormous calculations, thereby producing a problem in calculation speed. However, no attempt has been made to solve the periodic boundary condition by a hardware approach.

SUMMARY OF THE INVENTION

Accordingly, it is an object of the invention to provide a device in which the particle nearest to particle i is selected from particle j and reflected images of the particle j, and the difference between coordinates of the selected one and those of particle i is calculated at a high speed. Further, it is another object of the invention to provide a calculating device which is most suitable for calculating a difference of the periodic boundary condition. Furthermore, it is still another object of the invention to provide means for obtaining a force and a pressure.

The invention provides a coordinate difference calculating device for calculating differences $\Delta x_j = x_j - x_i$, $\Delta y_j = y_j - y_i$, and $\Delta z_j = z_j - z_i$ between coordinates $(x_i, y_i, z_i)$ and coordinates $(x_j, y_j, z_j)$ in an orthogonal coordinate system, including: an x-axis direction difference calculating circuit having means for judging whether $\Delta x_j$ is smaller than $-L_x/2$ or greater than $L_x/2$, $L_x$ being a value indicating a length of a side elongating in x-axis direction of a virtual rectangular parallelepiped, and means for adding $L_x$ to $\Delta x_j$ when $\Delta x_j$ is smaller than $-L_x/2$, and for subtracting $L_x$ from $\Delta x_j$ when $\Delta x_j$ is greater than $L_x/2$; a y-axis direction difference calculating circuit having means for judging whether $\Delta y_j$ is smaller than $-L_y/2$ or greater than $L_y/2$, $L_y$ being a value indicating a length of a side elongating in y-axis direction of the virtual rectangular parallelepiped, and means for adding $L_y$ to $\Delta y_j$ when $\Delta y_j$ is smaller than $-L_y/2$, and for subtracting $L_y$ from $\Delta y_j$ when $\Delta y_j$ is greater than $L_y/2$; and a z-axis direction difference calculating circuit having means for judging whether $\Delta z_j$ is smaller than $-L_z/2$ or greater than $L_z/2$, $L_z$ being a value indicating a length of a side elongating in z-axis direction of the virtual rectangular parallelepiped, and means for adding $L_z$ to $\Delta z_j$ when $\Delta z_j$ is smaller than $-L_z/2$, and for subtracting $L_z$ from $\Delta z_j$ when $\Delta z_j$ is greater than $L_z/2$.

Also, the invention provides a calculating device including: means for obtaining differences in coordinate axis directions $\Delta x_j = x_j - x_i$, $\Delta y_j = y_j - y_i$, and $\Delta z_j = z_j - z_i$ between coordinates $(x_i, y_i, z_i)$ of particle i and coordinates $(x_j, y_j, z_j)$ of particle j; calculating means coupled to receive the differences in coordinate axis directions $\Delta x_j$, $\Delta y_j$, and $\Delta z_j$, and a value F/r which is obtained by dividing the magnitude F of a force which is exerted by particle j onto particle i, by a distance r between the two particles, and for calculating coordinate axis components $F_x$, $F_y$, and $F_z$ of the force from the received values; first computing means for multiplying the x-axis component $F_x$ of the force by the difference $\Delta x_j$ of the x coordinate; second computing means for multiplying the y-axis component $F_y$ of the force by the difference $\Delta y_j$ of the y coordinate; and third computing means for multiplying the z-axis component $F_z$ of the force by the difference $\Delta z_j$ of the z coordinate.

BRIEF DESCRIPTION OF THE DRAWINGS

The accompanying drawings, which are incorporated in and constitute a part of this specification, illustrate embodiments of the invention and, together with the description, serve to explain the objects, advantages and principles of the invention. In the drawings.

DETAILED DESCRIPTION OF THE PREFERRED EMBODIMENTS

Hereinafter, features of the invention will be specifically described by illustrating embodiments with reference to the drawings.

Figure 1:
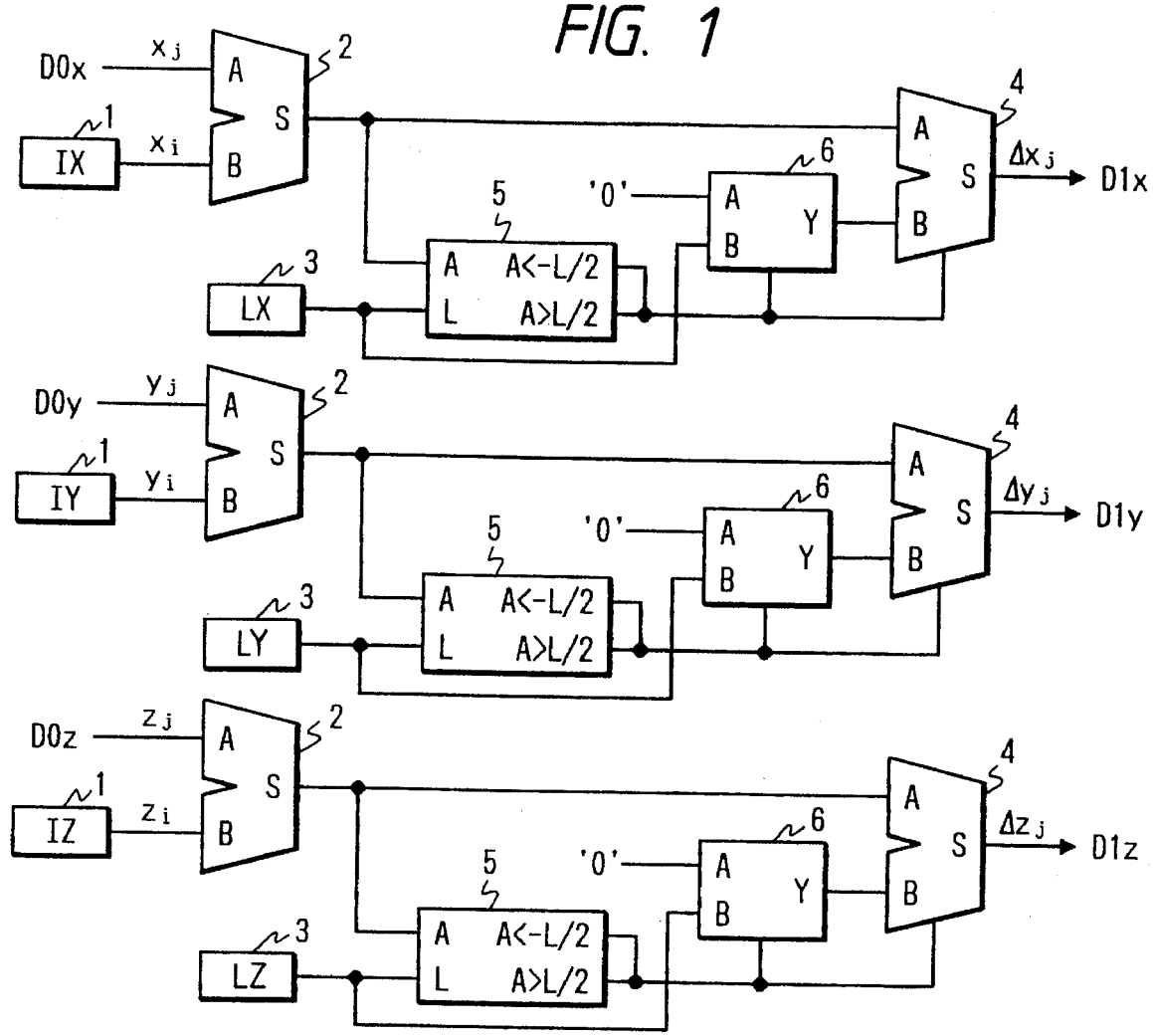
FIG. 1 is a block diagram showing a first embodiment of the invention.

FIG. 1 is a block diagram showing a first embodiment of the difference calculating device of the invention. As shown in FIG. 1, the difference calculating device includes: a register unit (designated by IX, IY, IZ in the figure) 1 for holding coordinates $(x_i, y_i, z_i)$ of particle i; a subtracting unit 2 for calculating differences between coordinates of particle i and coordinates $(x_j, y_j, z_j)$ of particle j which are supplied externally as inputs $D0_x$, $D0_y$, $D0_z$; a register unit (designated by LX, LY, LZ in the figure) 3 for respectively holding the lengths of the sides of the periodic boundary condition; an adding and subtracting unit 4 for producing outputs $D1_x$, $D1_y$, $D1_z$; a comparing unit 5 for determining whether a difference between the coordinates is smaller than $-(\frac{1}{2})$ of the length of one side of the periodic boundary condition or greater than $\frac{1}{2}$ of the length; and a selecting unit 6.

In FIG. 1, differences between the x-, y-, and z-coordinates are simultaneously obtained, and therefore three sets of the above-mentioned units are provided.

The operation of the device of FIG. 1 will be described with respect to the x-coordinate. X-coordinates $x_j$ of particle j and its reflected images are sequentially supplied from a device, which is not shown, to an input terminal A of the subtracting unit 2. X-coordinate $x_i$ of particle i which is previously stored in the register unit 1 by a device, which is not shown, is supplied to an input terminal B of the subtracting unit 2. In the subtracting unit 2, the data of the input terminal B is subtracted from the data of the input terminal A to obtain $\Delta x_j = x_j - x_i$. In the case where the periodic boundary condition is not used, the selecting unit 6 always selects the input terminal A, the adding and subtracting unit 4 conducts the adding operation, and therefore $\Delta x_j$ is obtained as it is at the output terminal $D1_x$.

In the case where the periodic boundary condition is used, the functions of the adding and subtracting unit 4 and the selecting unit 6 are switched as shown in Table 1 depending on the comparison result of the comparing unit 5.

TABLE 1

| Output of A<−L/2 | Output of A>L/2 | Selecting Unit 6 | Adding and Subtracting Unit 4 |
| --- | --- | --- | --- |
| 1 | 0 | Select Input B | Addition |
| 0 | 0 | Select Input A | Addition |
| 0 | 1 | Select Input B | Subtraction |

According to the functions, when $\Delta x_j$ is smaller than $-L_x/2$, $L_x$ is added to $\Delta x_j$, and when $\Delta x_j$ is greater than $L_x/2$, $L_x$ is subtracted from $\Delta x_j$. When $\Delta x_j$ is between $-L_x/2$ and $L_x/2$, $\Delta x_j$ is output as it is.

As a result of this process, the particle which is nearest in the x-axis direction to particle i is selected from particle j and its reflected images, and $\Delta x_j$ is converted to the difference between the x-coordinate of the selected particle and that of particle i.

Also with respect to the y- and z-coordinates, the device operates in the same manner as described above. Accordingly, the particle which is nearest to particle i in all the x-, y-, and z-axis directions is selected, and the differences between coordinates of the selected particle and those of particle i are obtained.

Figure 2:
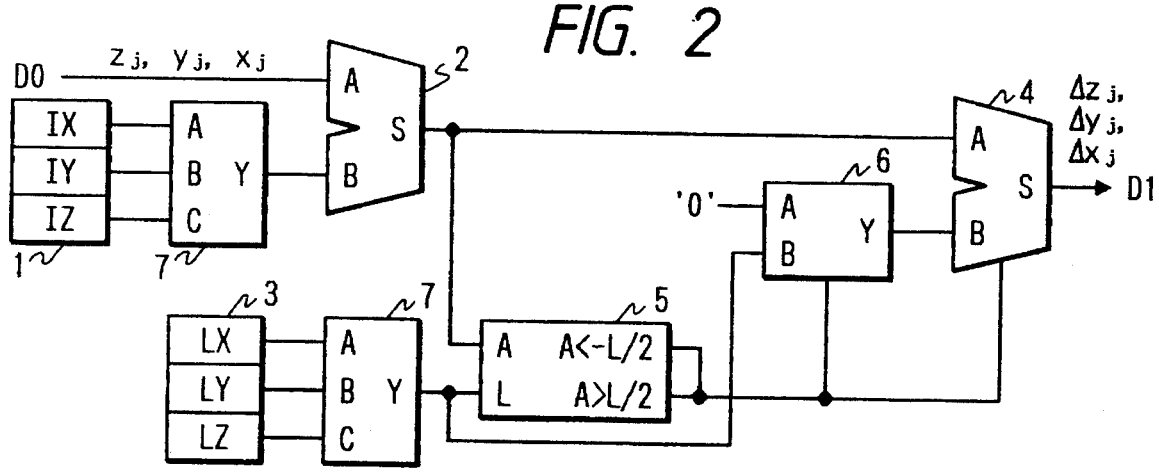
FIG. 2 is a block diagram showing a second embodiment of the invention.
Figure 3:
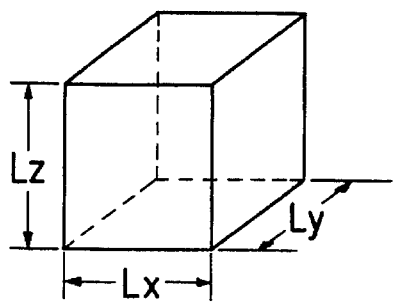
FIG. 3 is a view illustrating a periodic boundary of a rectangular parallelepiped.
Figure 4:
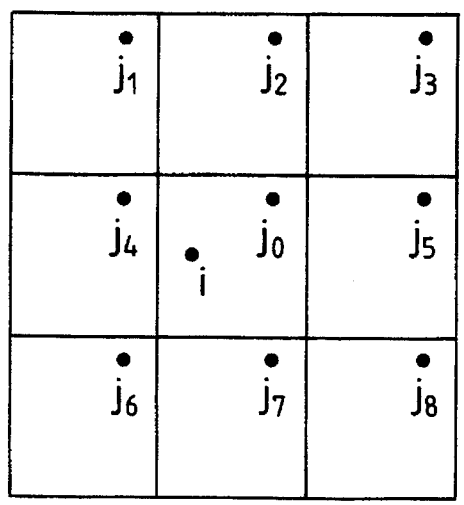
FIG. 4 is a view two-dimensional view illustrating an original rectangular parallelepiped and reflected images surrounding it.
Figure 5:
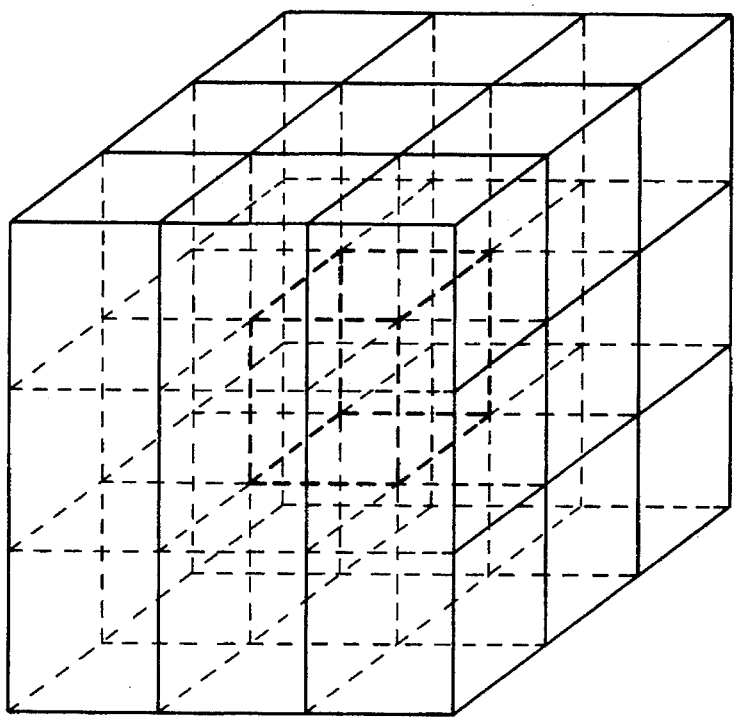
FIG. 5 is a view three-dimensional view illustrating the original rectangular parallelepiped and reflected images surrounding it.

FIG. 2 shows a second embodiment of the invention. In the second embodiment, portions corresponding to those of the first embodiment shown in FIG. 1 are designated by the same reference numerals. In the second embodiment, two sets of register selecting unit 7 are provided, and the subtracting unit 2, the adding and subtracting unit 4, the comparing unit 5, etc. are used in a time sharing manner.

When the periodic boundary condition can be regarded as a cube, the first and second embodiments can be modified so that only one set of the register unit 3 is provided. In the embodiments described above, coordinate values of particle i are subtracted from those of particle j. Alternatively, coordinate values of particle j may be subtracted from those of particle i.

In each of the first and second embodiments shown in FIGS. 1 and 2, a result is obtained at the output terminal of the adding and subtracting unit 4 when a certain time is elapsed after data are input to the input terminal A of the subtracting unit 2. In the case where the value of the delay time is greater than a desired value, latch means may adequately be disposed at the output terminals of the subtracting unit 2, the comparing unit 5, the adding and subtracting unit 4, and the like, so that a pipeline processing is conducted.

As described above, according to the invention, the comparing unit for checking the difference between coordinates of particle j and those of particle i to judge whether it is smaller than $-(\frac{1}{2})$ of the length of one side of a periodic boundary condition or greater than $\frac{1}{2}$ of the length is provided. In accordance with the output of the comparing unit, the length of one side of the periodic boundary condition is added to or subtracted from the coordinate difference. Therefore, the invention achieves the effect that the particle which is nearest to particle i can automatically be selected from particle j and its reflected images, and the difference between coordinates of the selected one and those of particle i can be obtained at high speed.

Next, features of the invention will be specifically described by illustrating a third embodiment with reference to the drawings.

Figure 6:
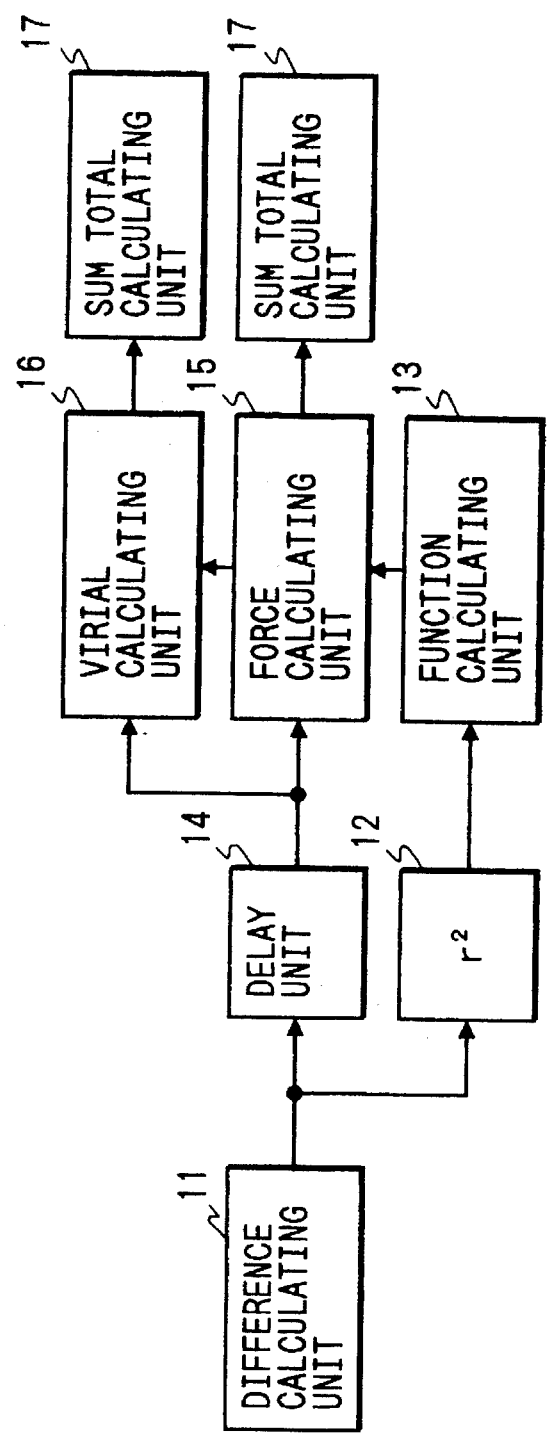
FIG. 6 is a block diagram showing a third embodiment of the invention.

First, the basic configuration of the invention will be described. As shown in FIG. 6, the calculating device of the invention includes: a difference calculating unit 11 for calculating differences between coordinates of two particles i and j; a unit 12 for calculating a square of the particle distance r from the differences between coordinates; a function calculating unit 13 for calculating a value which is obtained by dividing the absolute value F of a force acting between the two particles by r; a delay unit 14 for delaying the differences between coordinates; a force calculating unit 15 for calculating coordinate axis components of the force; a virial calculating unit 16 for calculating a virial; and a sum total calculating unit 17 for calculating a sum total of forces and that of virials. Here, a virial is calculated by multiplying components of a force by differences between coordinates, in order to obtain a pressure. In particular, virial is defined as half the product of the stress due to the attraction or repulsion between two particles in space multiplied by the distance between them or, in the case of more than two particles, half the sum of such products taken for the entire system (Webster's Third New International Dictionary of the English Language Unabridged, 1981).

Figure 7:
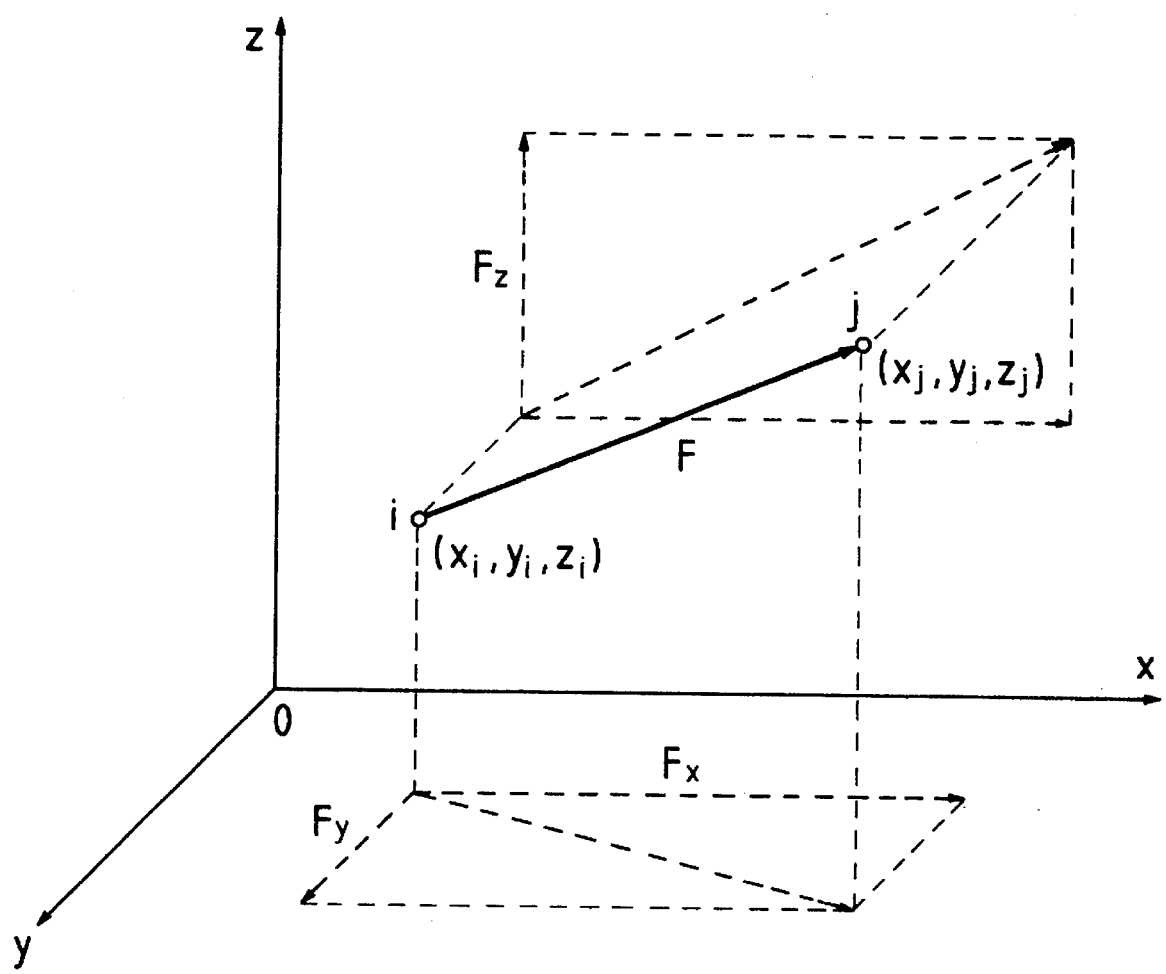
FIG. 7 is a diagram showing a force acting between two particles.

First, the manner of obtaining a force will be described with reference to FIG. 7. It is assumed that coordinates of particle i are indicated by $(x_i, y_i, z_i)$ and coordinates of particle j by $(x_j, y_j, z_j)$. The coordinate difference calculating unit 11 conducts the following calculations:

$$\Delta x_j = x_j - x_i$$

$$\Delta y_j = y_j - y_i$$

$$\Delta z_j = z_j - z_i$$

A square of the particle distance r is calculated by the unit 12 from the following expression:

$$r^2 = (\Delta x_j)^2 + (\Delta y_j)^2 + (\Delta z_j)^2$$

A force acting between two particles can be given by various function forms depending on the kind of the force and that of the particles. In any case, when r is determined, the value of the force is uniquely determined. Moreover, r is positive. When $r^2$ is determined, therefore, the value of r is uniquely determined. Accordingly, the force can be derived from $r^2$ using a lookup table.

When the magnitude of a force vector F is indicated by F, the coordinate axis components $F_x$, $F_y$, and $F_z$ are expressed as follows:

$$F_x = F \times (\Delta x_j/r) = (F/r) \times \Delta x_j$$

$$F_y = F \times (\Delta y_j/r) = (F/r) \times \Delta y_j$$

$$F_z = F \times (\Delta z_j/r) = (F/r) \times \Delta z_j$$

Accordingly, the function calculating unit 13 calculates F/r from $r^2$.

Since a considerably long calculation time is consumed until F/r is obtained from the differences between coordinates, the differences between coordinates are delayed by the delay unit 14. The force calculating unit 15 multiplies F/r obtained in the calculating unit 13 by the differences between coordinates which have been delayed by the delay unit 14, thereby calculating the components of the force in coordinate axis directions.

The pressure can be calculated in accordance with the virial theorem. This calculation is described in detail in technical books (for example, "Computer Simulation", Asakura Shoten, pp. 54–57), and therefore its detail description is omitted. In conclusion, components of the force are multiplied by the differences between coordinates as follows:

$$V_x = F_x \times \Delta x_j$$

$$V_y = F_y \times \Delta y_j$$

$$V_z = F_z \times \Delta z_j$$

and the pressure can be calculated from these values. This calculation is conducted by the unit 16 for calculating a virial. The force which is exerted by particle j onto particle i, and the virial are obtained in this way.

The force which actually acts on particle i is a sum total of forces which are exerted by all particles other than particle i onto particle i. The sum total calculation is conducted by the sum total calculating unit 17. In the same manner, a sum total of virials is calculated by another sum total calculating unit 17.

Figure 8:
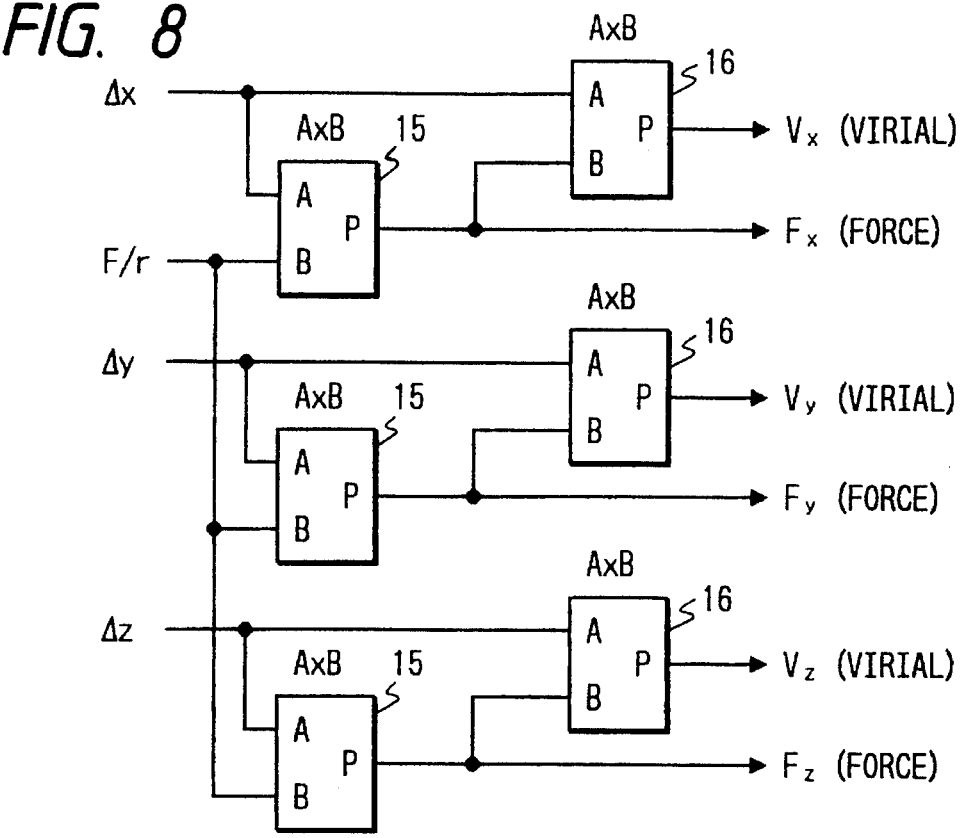
FIG. 8 is a block diagram showing an example of portions for calculating a force and a virial in the third embodiment.

FIG. 8 shows an example of the force calculating unit 15 and the virial calculating unit 16. In this example, six multiplying units are used in order to simultaneously calculate coordinate components.

Figure 9:
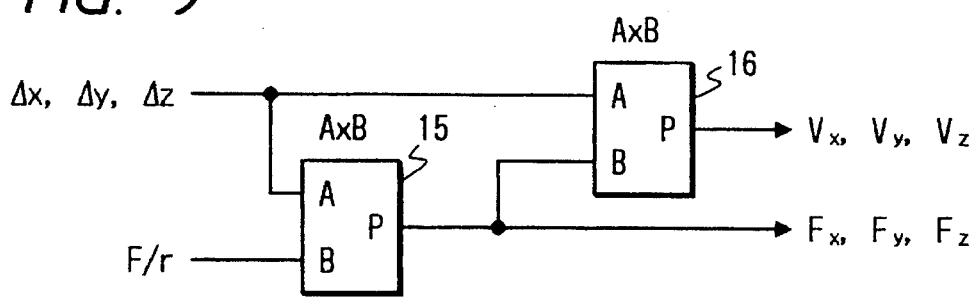
FIG. 9 is a block diagram showing another example of portions for calculating a force and a virial in the third embodiment.

FIG. 9 shows another example of the force calculating unit 15 and the virial calculating unit 16. In this example, two multiplying units are used in a time sharing manner so as to calculate coordinate components.

Figure 11:
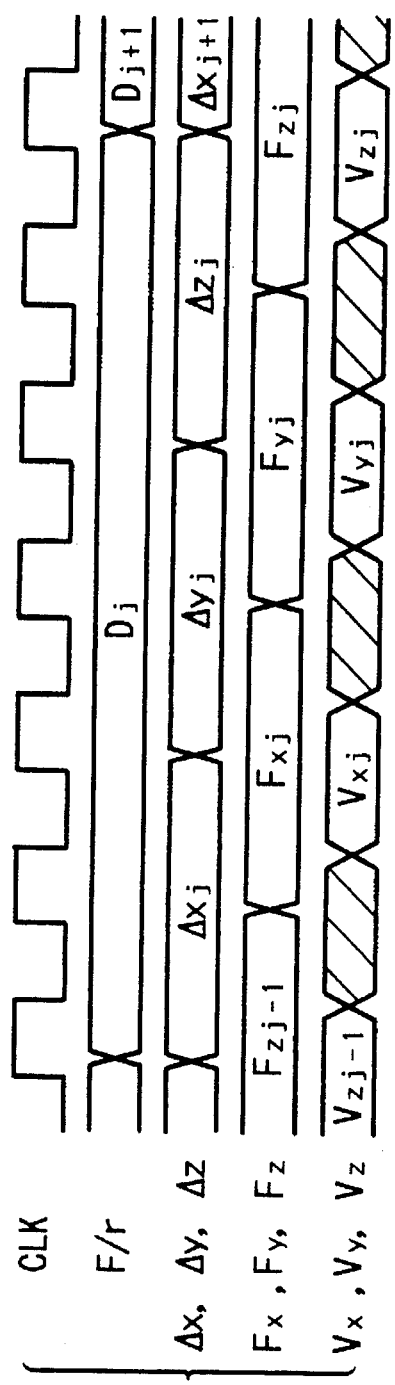
FIG. 11 is a timing chart showing the operation of the portions for calculating a force and a virial which are shown in FIG. 10.
Figure 10:
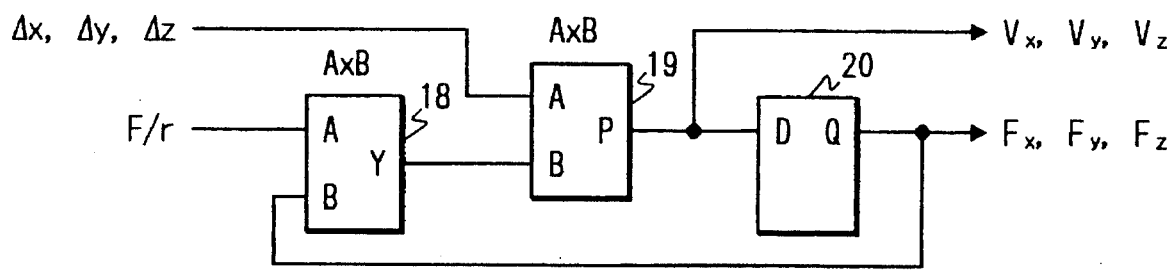
FIG. 10 is a block diagram showing still another example of portions for calculating a force and a virial in the third embodiment.

In FIG. 10, one multiplying unit is used in a time sharing manner so that calculations of components of a force and a virial are dividedly conducted in six calculation steps. In this case, the force calculating unit 15 and the virial calculating unit 16 are realized by a multiplying unit 19. Reference numeral 18 designates a unit for selectively outputting either F/r or force components, and 20 designates a latch unit. An example of calculation timing in this case is shown in FIG. 11. In the figure, CLK indicates a master clock signal.

In the examples shown in FIGS. 8 and 9, when data are applied to the input terminal of the force calculating unit 15, results are obtained at the output terminals of the force calculating unit 15 and the virial calculating unit 16 after the elapse of a certain time. In the case where the value of the delay time is greater than a desired value, latch means may be adequately disposed at the output portions of the force calculating unit 15 and the virial calculating unit 16 so that a pipeline processing is conducted.

As described above, according to the invention, components of a virial are allowed to be calculated at the same time with the calculation of a force, by additionally providing three to one multiplying unit or by using one multiplying unit in a time sharing manner. Therefore, the invention provides calculating means which can execute calculation of molecular dynamics at high speed in which a pressure calculation must be conducted.

What is claimed is:

1. A device for aiding in the making of determinations of properties of matter based on calculation of differences $\Delta x_j = x_j - x_i$, $\Delta y_j = y_j - y_i$, and $\Delta z_j = z_j - z_i$ between respective first particle coordinates of i having $(x_i, y_i, z_i)$ coordinate signals and respective second particle coordinates of j having $(x_j, y_j, z_j)$ coordinate signals in an orthogonal coordinate system, where i is an arbitrary point and j is one of inner points each regularly located within each of virtual rectangular parallelepipeds regularly stacked, j being located in a same rectangular parallelepiped as the point of i is located, and generating differences $\Delta x_j = x_j - x_i$, $\Delta y_j = y_j - y_i$, $\Delta z_j = z_j - z_i$, where $x_j$ is a coordinate of the nearest point among said inner points from said point of i with respect to an x-axis, $y_j$ is a coordinate of the nearest point among said inner points from said point of i with respect to an y-axis, and $z_j$ is a coordinate of the nearest point among said inner points with respect to a z-axis, comprising:

an x-axis circuit, responsive to the $x_i$ and $x_j$ signals, comprising:
   a first circuit for receiving the $x_i$ coordinate signal and the $x_j$ coordinate signal and generating the $\Delta x_j$;
   a comparison circuit for comparing the $x_i$ and $x_j$ signals and determining whether the $\Delta x_j$ is less than a first set value $-L_x/2$ corresponding to a length of a side of the virtual rectangular parallelepiped or greater than a second set value $L_x/2$ corresponding to the length of the side of the virtual rectangular parallelepiped, $L_x$ being a value indicating the length of an elongated side in the x-axis direction of the virtual rectangular parallelepiped;
   an adder circuit for receiving the $L_x$ and $\Delta x_j$ and adding the $L_x$ to $\Delta x_j$ and outputting a result as said difference $\Delta x_j = x_j - x_i$ when $\Delta x_j$ is less than $-L_x/2$;
   a subtraction circuit for receiving the $L_x$ and $\Delta x_j$ and subtracting $L_x$ from $\Delta x_j$ and outputting a result as said difference $\Delta x_j = x_j - x_i$ when $\Delta x_j$ is greater than $L_x/2$; and
   said first circuit outputting the $\Delta x_j$ as said difference $\Delta x_j = x_j - x_i$ when $\Delta x_j$ is equal to or more than $-L_x/2$ and equal to or less than $Li/2$;

a y-axis circuit, responsive to the $y_i$ and $y_j$ signals, comprising:
   a second circuit for receiving the $y_i$ coordinate signal and the $y_j$ coordinate signal and generating the $\Delta y_j$;
   a comparison circuit for comparing the $y_i$ and $y_j$ signals and determining whether the $\Delta y_j$ is less than a first set value $-L_y/2$ corresponding to a length of a side of the virtual rectangular parallelepiped or greater than a second set value $L_y/2$ corresponding to the length of the side of the virtual rectangular parallelepiped, $L_y$ being a value indicating the length of an elongated side in the y-axis direction of the virtual rectangular parallelepiped;
   an adder circuit for receiving the $L_y$ and $\Delta y_j$ and adding the $L_y$ to $\Delta y_j$ and outputting a result as said difference $\Delta y_j = y_j - y_i$ when $\Delta y_j$ is less than $-L_y/2$;
   a subtraction circuit for receiving the $L_y$ and $\Delta L_y$ and $\Delta y_j$ and subtracting $L_y$ from $\Delta y_j$ and outputting a result as said difference $\Delta y_j = y_j - y_i$ when $\Delta y_j$ is greater than $L_y/2$; and
   said second circuit outputting the $\Delta y_j$ as said difference $\Delta y_j = y_j - y_i$ when $\Delta y_j$ is equal to or more than $-L_y/2$ and equal to or less than $L_y/2$; and a z-axis circuit, responsive to the $z_i$ and $z_j$ signals, comprising:
   a third circuit for receiving the $z_i$ coordinate signal and the $z_j$ coordinate signal and generating the $\Delta z_j$;
   a comparison circuit for comparing the $z_i$ and $z_j$ signals and determining whether the $\Delta z_j$ is less than a first set value $-L_z/2$ corresponding to a length of a side of a virtual rectangular parallelepiped or greater than a second set value $L_z/2$ corresponding to the length of the side of the virtual rectangular parallelepiped, $L_z$ being a value indicating the length of an elongated side in the z-axis direction of the virtual rectangular parallelepiped;
   an adder circuit for receiving the $L_z$ and $\Delta z_j$ and adding the $L_z$ to $\Delta z_j$ and outputting a result as said difference $\Delta z_j = z_j - z_i$ when $\Delta z_j$ is less than $-L_z/2$;
   a subtraction circuit for receiving the $L_z$ and $\Delta z_j$ and subtracting $L_z$ from $\Delta z_j$ and outputting a result of said difference $\Delta z_j = z_j - z_i$ when $\Delta z_j$ is greater than $L_z/2$; said third circuit outputting the $\Delta z_j$ as said difference $\Delta z_j = z_j - z_i$ when $\Delta z_j$ is equal to more than $-L_z/2$ and equal to or less than $L_z/2$.

2. The device according to claim 1, wherein said x-axis circuit, y-axis circuit, and z-axis circuit are formed as three independent circuits simultaneously conducting calculations.

3. The device according to claim 1, wherein said x-axis circuit, y-axis circuit, and z-axis circuit are formed as a single circuit sequentially conducting calculations in a time sharing manner.

4. A calculating device comprising:

means for generating signals corresponding to coordinate axis components $(x_i, y_i, z_i)$ of a particle i and $(x_j, y_j, z_j)$ of a particle j;

means for obtaining differences between corresponding component signals for each coordinate axis $\Delta x_j = x_j - x_i$, $\Delta y_j = y_j - y_i$, and $\Delta z_j = z_j - z_i$ to determine differences between the coordinates $(x_i, y_i, z_i)$ of the particle i and the coordinates $(x_j, y_j, z_j)$ of the particle j;

a first circuit coupled to the obtaining means and receiving the differences of each of the coordinate axis components $\Delta x_j$, $\Delta y_j$, and $\Delta z_j$;

a second circuit for obtaining a value F/r, where F is a magnitude of force exerted by particle j onto particle i and r is a distance between the two particles i and j, the second circuit including:

a divider circuit for dividing the magnitude F by the distance r between the two particles, and a force component calculation circuit, in response to the value F/r from the divider circuit and the differences of each of the coordinate axis components $\Delta x_j$, $\Delta y_j$, and $\Delta z_j$ from the first circuit, for calculating coordinate axis components $F_x$, $F_y$, and $F_z$ of the force exerted by particle j onto particle i;

first computing means for multiplying the x-axis component $F_x$ of the force by the difference $\Delta x_j$ of the x coordinate;

second computing means for multiplying the y-axis component $F_y$ of the force by the difference $\Delta y_j$ of the y coordinate; and third computing means for multiplying the z-axis component $F_z$ of the force by the difference $\Delta z_j$ of the z coordinate.

5. The calculating device according to claim 4, wherein said first, second, and third computing means are formed as three independent circuits simultaneously conducting calculations.

6. The calculating device according to claim 4, wherein said first, second, and third computing means are formed as a single circuit sequentially conducting calculations in a time sharing manner.

7. The calculating device according to claim 4, wherein said force component calculation circuit for calculating the coordinate axis components of the force includes fourth, fifth, and sixth computing means for multiplying the differences in coordinate axis component signals $\Delta x_j$, $\Delta y_j$, $\Delta z_j$ by the value F/r, thereby obtaining the coordinate axis components $F_x$, $F_y$, $F_z$ of the force.

8. The calculating device according to claim 7, wherein said first, second, third, fourth, fifth, and sixth computing means are formed as a single circuit sequentially conducting calculations in a time sharing manner.

9. A calculating device for aiding in the making of determinations of properties of matter through calculation of differences, said calculating device comprising:

a difference circuit for generating difference signals $\Delta x_j = x_j - x_i$ and $\Delta y_j = y_j - y_i$ between first particle coordinates of i having ($x_i$, $y_i$) coordinate signals and second particle coordinates of j having ($x_j$, $y_j$) coordinate signals in an orthogonal coordinate system, where i is an arbitrary point and j is one of inner points each regularly located within each of virtual rectangular parallelepipeds regularly stacked, j being located in a same rectangular parallelepiped as the point of i is located, and generating differences $\Delta x_j = x_j - x_i$ and $\Delta y_j = y_j - y_i$, where $x_j$ is a coordinate of the nearest point among said inner points from said point of i with respect to an x-axis and $y_j$ is a coordinate of the nearest point among said inner points with respect to a y-axis;

an x-axis circuit, responsive to the $x_i$ and $x_j$ signals, comprising:

a first circuit for receiving the $x_i$ coordinate signal and the $x_j$ coordinate signal and generating the $\Delta x_j$;

a comparison circuit for comparing the $x_i$ and $x_j$ signals and determining whether the $\Delta x_j$ is less than a first set value $-L_x/2$ corresponding to a length of a side of the virtual rectangular parallelepiped or greater than a second set value $L_x/2$ corresponding to the length of the side of the virtual rectangular parallelepiped, $L_x$ being a value indicating the length of an elongated side in the x-axis direction of the virtual rectangular parallelepiped;

an adder circuit for receiving the $L_x$ and $\Delta x_j$ and adding the $L_x$ to $\Delta x_j$ and outputting a result as said difference $\Delta x_1 = x_j - x_i$ when $\Delta x_j$ is less than $-L_x/2$;

a subtraction circuit for receiving the $L_x$ and $\Delta x_j$ and subtracting $L_x$ from $\Delta x_j$ and outputting a result as said difference $\Delta x_1 = x_j - x_i$ when $\Delta x_j$ is greater than $L_x/2$; and said first circuit outputting the $\Delta x_j$ as said difference $\Delta x_j = x_j - x_i$ when $\Delta x_j$ is equal to or more than $-L1/2$ and equal to or less than $L1/2$;

a y-axis circuit, responsive to the $y_i$ and $y_j$ signals, comprising:

a second circuit for receiving the $y_i$ coordinate signal and the $y_j$ coordinate signal and generating the $\Delta y_j$;

a comparison circuit for comparing the $y_i$ and $y_j$ signals and determining whether the $\Delta y_j$ is less than a first set value $-L_y/2$ corresponding to a length of a side of a virtual rectangular parallelepiped or greater than a second set value $L_y/2$ corresponding to the length of the side of the virtual rectangular parallelepiped, $L_y$ being a value indicating the length of an elongated side in the y-axis direction of the virtual rectangular parallelepiped;

an adder circuit for receiving the $L_y$ and $\Delta y_j$ and adding the $L_y$ to $\Delta y_j$ and outputting a result as said difference $\Delta y_j = y_j - y_i$ when $\Delta y_j$ is less than $-L_y/2$;

a subtraction circuit for receiving the $L_y$ and $\Delta y_j$ and subtracting $L_y$ from $\Delta y_j$ and outputting a result as said difference $\Delta y_j = y_j - y_i$ when $\Delta y_j$ is greater than $L_y/2$; and said second circuit outputting the $\Delta y_j$ as said difference $\Delta y_j = y_j - y_i$ when $\Delta y_j$ is equal to or more than $-L_y/2$ and equal to or less than $L_y/2$.

10. The device for calculating differences according to claim 9, wherein said x-axis circuit and said y-axis circuit are formed as two independent circuits simultaneously conducting calculations.

11. The device for calculating differences according to claim 9, wherein said x-axis circuit and y-axis circuit are formed as a single circuit sequentially conducting calculations in a time sharing manner.

* * * * *

UNITED STATES PATENT AND TRADEMARK OFFICE
CERTIFICATE OF CORRECTION

PATENT NO. : 5,572,447
DATED : November 5, 1996
INVENTOR(S) : Shinjiro TOYODA et al.

It is certified that error appears in the above-indentified patent and that said Letters Patent is hereby corrected as shown below:

Claim 1, column 7, line 42, "an y-axis" should read -- a y-axis --.

Claim 1, column 7, line 45, "$x_i$" (second occurrence) should read -- $x_j$ --.

Claim 1, column 7, line 60, "$\Delta x_j = x_j - x_j$" should read -- $\Delta x_j = x_j - x_i$ --.

Claim 1, column 7, line 66, "$-L_i/2$" should read -- $-L_x/2$ --.

Claim 1, column 7, line 67, "$L_i/2;$" should read -- $L_x/2;$ --.

Claim 9, column 10, line 16, "$\Delta x_1$" should read -- $\Delta x_j$ --.

Claim 9, column 10, line 19, "$\Delta x_1$" should read -- $\Delta x_j$ --.

Claim 9, column 10, line 22, "$-L1/2$" should read -- $-L_x/2$ --.

UNITED STATES PATENT AND TRADEMARK OFFICE
CERTIFICATE OF CORRECTION

PATENT NO. : 5,572,447
DATED : November 5, 1996
INVENTOR(S) : Shinjiro Toyoda, et. al.

It is certified that error appears in the above-indentified patent and that said Letters Patent is hereby corrected as shown below:

Claim 9, column 10, line 23, "L1/2" should read -- $L_x/2$ --.

Signed and Sealed this

First Day of July, 1997

Attest:

Attesting Officer

BRUCE LEHMAN

Commissioner of Patents and Trademarks